(12) United States Patent
Potter et al.

(10) Patent No.: US 7,862,543 B2
(45) Date of Patent: Jan. 4, 2011

(54) DRUG DELIVERY SYSTEM

(75) Inventors: David S. Potter, Cowes (GB); Charles D. Ogilvy Potter, Standlake (GB)

(73) Assignee: Glide Pharmaceutical Technologies Limited, London (GB)

( * ) Notice: Subject to any disclaimer, the term of this patent is extended or adjusted under 35 U.S.C. 154(b) by 1096 days.

(21) Appl. No.: 10/523,473

(22) PCT Filed: Jul. 18, 2003

(86) PCT No.: PCT/EP03/07859

§ 371 (c)(1),
(2), (4) Date: Jan. 3, 2006

(87) PCT Pub. No.: WO2004/014468

PCT Pub. Date: Feb. 19, 2004

(65) Prior Publication Data

US 2006/0161111 A1    Jul. 20, 2006

(30) Foreign Application Priority Data

Aug. 5, 2002    (GB) ................................. 2181265.1

(51) Int. Cl.
*A61M 5/20*    (2006.01)
*A61M 5/315*    (2006.01)
*A61M 5/00*    (2006.01)

(52) U.S. Cl. ...................... 604/138; 604/135; 604/136; 604/218; 604/232

(58) Field of Classification Search .................. 604/135, 604/136, 138, 139, 189, 200–206, 232, 235, 604/218

See application file for complete search history.

(56) References Cited

U.S. PATENT DOCUMENTS 1,819,415 A    8/1931    Harris (Continued)

FOREIGN PATENT DOCUMENTS

CA    1019638    10/1977

(Continued)

OTHER PUBLICATIONS

Co-Pending U.S. Appl. No. 10/489,625.

(Continued)

*Primary Examiner*—Nicholas D Lucchesi
*Assistant Examiner*—Victoria P Campbell
(74) *Attorney, Agent, or Firm*—Robert L. Kelly; Dickinson Wright PLLC

(57) ABSTRACT

A drug delivery system is disclosed which may be a throw-away or reusable device for delivery at least one drug to a patient. Also described is a method for administering a drug using said device and a packaged drug for use with said device. The drug delivery device (10) comprises a housing (12), a means (14) for generating a force capable of pushing a drug (16) from a packaging (18) into a human or animal body, a means (20) for transmitting said force to push the drug (16) from the packaging (18) into the human and animal body, and a means (38, 42*b*) for triggering the device. Where the device is a single use drug delivery system, a packaged drug (100) forms an integral part of the device. The packaged drug comprises a region (102) allowing it to be slidably mounted to the drug delivery device (10).

13 Claims, 4 Drawing Sheets

U.S. PATENT DOCUMENTS

| | | |
|---|---|---|
| 2,398,544 A | 4/1946 | Lockhart |
| 2,752,918 A | 7/1956 | Uytenbogaart |
| 3,616,758 A | 11/1971 | Komarov |
| 3,901,158 A | 8/1975 | Ferb |
| 3,948,263 A | 4/1976 | Drake |
| 3,982,536 A | 9/1976 | Krogseng et al. |
| 4,059,107 A | 11/1977 | Iriguchi et al. |
| 4,116,196 A | 9/1978 | Kaplan et al. |
| 4,326,524 A | 4/1982 | Drake |
| 4,419,936 A | 12/1983 | Coates et al. |
| 4,449,982 A | 5/1984 | Gould, III |
| 4,518,387 A | 5/1985 | Murphy et al. |
| 4,664,664 A | 5/1987 | Drake, Jr. |
| 4,790,824 A | 12/1988 | Morrow et al. |
| 4,808,184 A | 2/1989 | Tepic |
| 4,863,429 A | 9/1989 | Baldwin |
| 4,871,094 A | 10/1989 | Clements et al. |
| 4,968,302 A | 11/1990 | Schluter et al. |
| 5,092,842 A | 3/1992 | Bechtold et al. |
| 5,116,313 A | 5/1992 | McGregor |
| 5,206,024 A | 4/1993 | Peery et al. |
| 5,354,287 A | 10/1994 | Wacks |
| 5,360,410 A | 11/1994 | Wacks |
| 5,542,920 A | 8/1996 | Cherif Cheikh |
| 5,549,560 A | 8/1996 | Van de Wijdeven |
| 5,589,167 A | 12/1996 | Cleland et al. |
| 5,599,302 A | 2/1997 | Lilley et al. |
| 5,747,058 A | 5/1998 | Tipton et al. |
| 6,001,385 A | 12/1999 | Van De Wijdeven |
| 6,102,896 A | 8/2000 | Roser |
| 6,117,443 A | 9/2000 | Cherif-Cheikh |
| 6,120,786 A | 9/2000 | Cherif Cheikh |
| 6,203,521 B1 | 3/2001 | Menne et al. |
| 6,264,629 B1 | 7/2001 | Landau |
| 6,331,310 B1 | 12/2001 | Roser et al. |
| 6,375,971 B1 | 4/2002 | Hansen |
| 6,586,006 B2 | 7/2003 | Roser et al. |
| 6,680,692 B2 | 1/2004 | Solbach |
| 6,689,093 B2 | 2/2004 | Landau |
| 6,783,509 B1 | 8/2004 | Landau et al. |

FOREIGN PATENT DOCUMENTS

| | | |
|---|---|---|
| DE | 3644984 A1 | 7/1988 |
| EP | 0008636 | 6/1982 |
| EP | 0139286 | 5/1985 |
| EP | 0119286 | 12/1987 |
| EP | 0276158 | 7/1988 |
| EP | 0427457 | 5/1991 |
| EP | 0518561 | 12/1992 |
| EP | 0409365 | 4/1994 |
| EP | 0595508 | 5/1994 |
| EP | 0666084 | 8/1995 |
| EP | 0 879 609 A | 11/1998 |
| FR | 1014881 | 6/1952 |
| FR | 1049564 | 12/1953 |
| FR | 2627698 | 3/1988 |
| FR | 2 749 764 A | 12/1997 |
| GB | 993309 | 5/1965 |
| GB | 2193644 | 12/1988 |
| GB | 2239180 | 6/1991 |
| GB | 2365100 | 2/2002 |
| WO | WO 94/07553 | 4/1994 |
| WO | WO 94/22423 | 10/1994 |
| WO | WO 96/40351 | 12/1996 |
| WO | WO 00/62734 | 10/2000 |
| WO | WO 02/48654 | 6/2002 |
| WO | WO 2006082439 | 8/2006 |

OTHER PUBLICATIONS

Co-Pending U.S. Appl. No. 10/238,415.
European Patent Office, Search and Examination Report, Application GB0605772.3, Apr. 26, 2006.

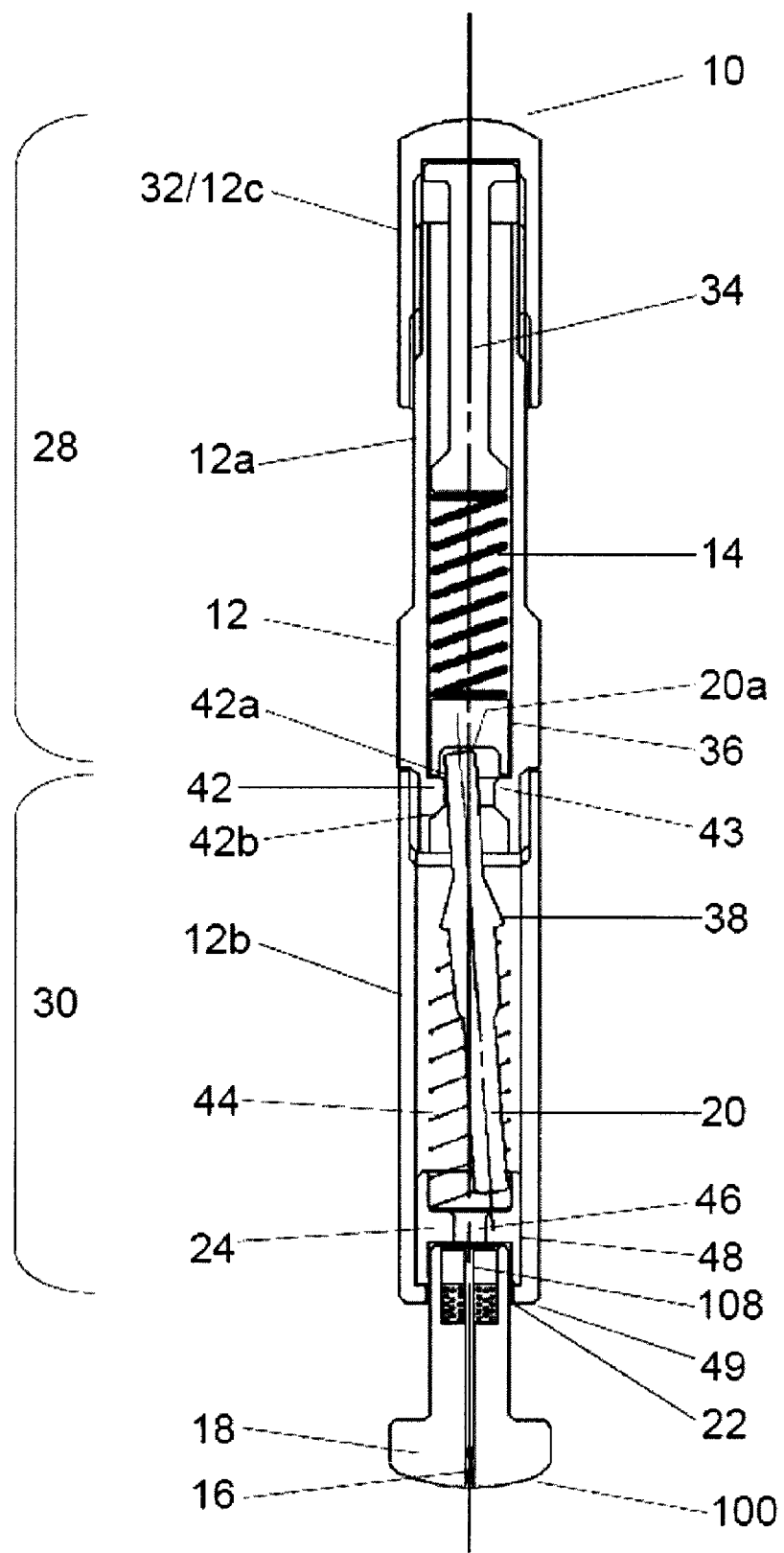

DRUG DELIVERY SYSTEM

FIELD OF THE INVENTION

The present invention relates to a novel drug delivery system. More particularly, the invention relates to a throwaway or reusable device for delivering at least one therapeutic compound, or a formulation comprising the at least one therapeutic compound (hereafter drug) to a patient, and a method for administering a drug to a patient using said device. It also relates to a packaged drug for use with said device.

BACKGROUND TO THE INVENTION

The applicant's earlier UK application no 0121914.6 discloses a novel drug delivery technology and device for delivering an injectate. The device is intended to deliver a pioneer projectile and a following drug, and comprises an outer housing or holder, the lowermost end of which is slidably mounted within the uppermost end. At the lowermost end is fitted a disposable component, such as, for example, a drug cassette. The drug cassette is screwed into the lowermost end of the inner housing. The drug cassette comprises a casing, having a central aperture or chamber in which is mounted an injectate comprising a pioneer projectile and a formulate. A large headed ejector pin is positioned above the injectate, and when contacted by a striker in the device is pushed into a patient.

The applicant's earlier application is based on their recognition that a pioneer projectile can be used as a means for introducing medicaments in forms other than as a free flowing, non viscous liquid.

In it, they describe a method of delivering at least one therapeutic compound, or a formulation containing the at least one therapeutic compound to a human or animal in the form of a needleless injection comprising:
  i) Penetrating the skin with a pioneer projectile which is left in the human or animal; and
  ii) Introducing directly, or substantially directly, behind the pioneer projectile, the at least one therapeutic compound or the formulation containing the at least one therapeutic compound, which at least one therapeutic compound or the formulation containing the at least one therapeutic compound is provided in a contained state.

By contained state is meant either:
  i) As a liquid contained by a membrane;
  ii) As a liquid with a viscosity of at least 5000 centipoises (the viscosity of honey), more particularly at least 50,000 (the consistency of mayonnaise) and most preferably still at least 100,000 (the consistency of peanut butter), such that the liquid has characteristics more akin to a solid than a liquid i.e. they have a definite shape as well as volume (and are not readily free flowing);
  iii) As a semi-solid (having a viscosity and rigidity intermediate that of a solid or a liquid);
  iv) As a paste (having a soft malleable consistency);
  v) As a gel (a liquid dispersed in a solid); which materials can all be considered to have a degree of stiffness; or
  vi) As a solid (a state in which the matter retains its own shape).

Introducing a medicament in such a contained state has advantages in that splash back and seepage can be avoided and more controlled dosages delivered when compared to a following non viscous liquid formulation. The viscous, semi solid or solid nature of the medicament ensures that the pioneer projectile is pushed to the requisite depth and is followed by the medicament rather than seeping around the sides of the projectile. The semi solid formulations, gels, pastes and solids are also generally more stable than liquid formulations and are more patient compliable.

By introducing the medicament in a form other than as a non viscous liquid behind a pioneer projectile, it is possible to tailor the characteristics of the medicament for optimum pharmacokinetic delivery rather than for penetration.

Similarly the pioneer projectile can be developed to have optimised penetrating capabilities independent of the medicament.

Preferably the pioneer projectile is independent of the at least one therapeutic compound or the formulation containing the at least one therapeutic compound.

Alternatively, the pioneer projectile is independent of, yet forms an integral part of the at least one therapeutic compound or the formulation containing the at least one therapeutic compound.

Most preferably the pioneer projectile forms a head to the at least one therapeutic compound or the formulation containing the at least one therapeutic compound.

The at least one therapeutic compound or the formulation containing the at least one therapeutic compound can take a number of forms.

In one embodiment the at least one therapeutic compound or the formulation containing the at least one therapeutic compound is a liquid contained in a water soluble, lipid soluble or otherwise biodegradable membrane.

In another embodiment the at least one therapeutic compound or the formulation containing the at least one therapeutic compound is provided in a solid form such as, for example, crystals, particles, granules, beads, rods, discs or a combination thereof.

In yet another embodiment the at least one therapeutic compound or the formulation containing the at least one therapeutic compound is provided as a viscous liquid, semi solid, gel or paste which may be further supported, if desirable, by a water soluble lipid soluble or otherwise biodegradable membrane.

In the method of their earlier described invention the skin is penetrated and the therapeutic compound administered at a low velocity. By low velocity is meant less than 100 m/s. Preferably the velocity is less than 10 m/s.

Since the injectate is pushed at a low velocity rather than fired at a high velocity it is possible to ensure that the dosage is always delivered to the correct (and same) depth under the skin. This means that the system can be used on different skin types and skin locations and the dosage will still be delivered to the same depth.

This earlier application also describes novel pioneer projectiles comprising:
  i) A first "penetrating" face which in use penetrates the human or animal's skin; and
  ii) Remote from the first face a second "driven" face which in the course of injection is the face upon which a driving force is exerted through the therapeutic compound or therapeutic compound containing formulation; characterised in that said pioneer projectile has an aspect ratio (width to height) of less than 1:10.

Because the pioneer projectile were developed separately of the medication, it was possible to make them less than 10 mm in length and optimise their shape such that it functions as a leading head or tip for a following formulation, the two components forming an injectate.

Preferably the pioneer projectile is water soluble, lipid soluble or otherwise biodegradable.

Preferably the pioneer projectile has an aspect ratio of less than 1:8, preferably less than 1:6, more preferably less than 1:4, more preferably still less than 1:3, and most preferably about 1:1.5.

Preferably the pioneer projectile is less than 3 mm in width, more preferably still about 1 mm in width.

Preferably the pioneer is less than 10 mm in height, more preferably about 1.5 to 2 mm in height. By reducing the height to a minimum it is possible to maximise the amount of therapeutic compound being injected. In this regard it should be noted that if the combined pioneer projectile and following drug formulation is too long it might not be possible to deliver the drug to the optimum depth.

In one embodiment, the pioneer projectile is free of any therapeutic compound. In another embodiment it comprises at least one therapeutic compound. Thus, for example it might be beneficial to include, for example an antibiotic in the pioneer projectile or have it release a therapeutic compound at a different rate to the formulation in, for example, the case of insulin injections.

The skin penetrating face of the pioneer projectile preferably comprises a cutting element to facilitate entry. This may take the form of a sharp point or an oblique edge. Alternatively the skin penetrating face may be blunt or gently curved.

In one embodiment the face for contacting the therapeutic compound or therapeutic compound containing formulation in a contained state is flat. Alternatively it may be concave or otherwise hollowed to facilitate pushing and formulation containment.

The pioneer projectile may be made of any suitable material. Suitable materials are those hard and rigid enough to facilitate penetration at low velocities. More preferred are materials, which are also water soluble, lipid soluble or otherwise biodegradable.

Preferred materials include glassy materials e.g. the sugar glasses as noted in WO 98/41188 which materials are included herein by reference.

In some circumstances the pioneer projectile may comprise a barrier material over at least the face that contacts the therapeutic compound in a contained state or vice versa such that the respective components will not react with one another.

The earlier application also discloses novel formulations. They comprise a therapeutic compound or therapeutic compound containing formulation which is held in a contained state and adapted for introduction into a human or animal in the form of a needleless injection behind a pioneer projectile.

Preferably the formulation comprises less than 50 mg of therapeutic compound in a volume of less than 50 mm$^3$ more preferably less than 10 mg of therapeutic compound in a volume of less than 10 mm$^3$.

The therapeutic compound or therapeutic compound containing formulation may be provided as a liquid contained in water soluble, lipid soluble or otherwise biodegradable membrane.

In an alternative embodiment the therapeutic compound or therapeutic compound containing formulation is provided in a solid form comprising for example crystals, particles, granules, beads, rods, discs or a combination thereof which are generally likely to be more stable than traditional non-viscous liquid formulations with a viscosity similar to that of water e.g. 1 Centipoises or glucose e.g. 500 Centipoises.

In a preferred embodiment the therapeutic compound or therapeutic compound containing formulation is provided as a semi solid, gel or paste. In this form it is particularly patient compliant and the therapeutic compound is generally likely to be more stable than if it were in a traditional non-viscous liquid formulation.

Where the therapeutic compound or therapeutic compound containing formulation is a viscous liquid, it preferably has a viscosity of at least 10,000 Centipoises more preferably at least 50,000 Centipoises and more preferably still at least 100,000 Centipoises.

The formulation may comprise an end piece beyond the therapeutic compound or therapeutic compound to ensure that the entire therapeutic compound enters the patient.

The therapeutic compound or therapeutic compound containing formulation may comprise a plurality of differently formulated elements.

The therapeutic compound or therapeutic compound containing formulation may be packaged in a cap, cartridge, carousel or cassette.

The applicant's earlier UK application no 0121914.6 also extends to an injectate comprising a pioneer projectile and a therapeutic compound or therapeutic compound containing formulation.

It discloses a needleless injectate for injection comprising:
a) A pioneer projectile; and
b) A therapeutic compound or therapeutic compound containing formulation which is held in a contained state behind the pioneer projectile.

These components are as previously described.

The pioneer projectile and therapeutic compound or therapeutic compound containing formulation may both be water soluble, lipid soluble or otherwise biodegradable to differing degrees.

The injectate may be contained/packaged in a cap, cartridge, carousel or cassette optionally together with a means, e.g. an ejector pin, for pushing the pioneer injectate out of its container.

Alternatively the pioneer projectile and the therapeutic compound or therapeutic compound containing formulation are contained/packaged in separate caps, cartridges, carousels or cassettes.

The present invention incorporates all of the disclosure from this earlier UK application no 0121914.6 by reference.

An aim of the present invention is to produce a simple, cheap drug delivery device which is adaptable and able to deliver a drug in the form of not only a needleless injectate but also other forms, such as, for example liquid formulations, and solid drug needles.

This aim is achieved by the provision of a device which is adapted to receive a packaged drug which is slidably mounted in the device such that in use the device is able to push a drug from its packaging, the packaged drug being packaged such that the drug, whatever it's form, can be pushed from its packaging by the device.

It is another and independent aim to package different drug forms for use with such a device.

This aim is achieved by the provision of a packaging adapted to be attached to the device and which comprises a channel housing the drug, and a drive pin or like element for pushing it out when actuated by the device.

There are many possible product applications for such a delivery device and they include therapeutic, prophylactic and diagnostic applications. Applications may be limited to those drugs that are administered in relatively low doses because of the dose limitations for each injection imposed by pushing. However, although each dose may be limited to less than 10 mg or a volume of less than 10 mm$^3$ it would be possible to administer more than one dose either concurrently or sequentially, if larger doses are required.

New laws in many states in the USA are declaring that safety needles must be used for injections whenever possible. These are needles that withdraw into a sheath as the needle is withdrawn from the patient so that the needle tip is not left exposed. This is to avoid the use of a conventional needle which can result in accidental needle stick injuries. A delivery system that either does not require a needle (or that incorporates a needle that retracts) would be beneficial for the US market as well as other parts of the world that will, no doubt, follow the lead of the Americans.

Particular applications where the technology might be very well suited include:

Vaccines:—Vaccinations are one of the common reasons for people to need an injection and many people would rather risk catching a disease than have to be injected with a standard needle and syringe. Children in particular can often have a needle phobia. Therefore a system that either does not incorporate a needle (or the needle is never seen by the patient) might help compliance with vaccines. In third world countries there is a great need for delivery systems for vaccines that do not involve needles. An added advantage of the new delivery system is that using a non liquid dose therapeutic compound should assist stability of the active compounds and therefore the cold chain storage requirements for the vaccine may be avoided.

Acute Emergencies:—The device is very quick and easy to use and therefore well suited for self administration as well as administration by an untrained assistant. There are a number of drugs, such as glucagon (hypoglycaemia), migraine treatments or adrenalin (anaphylactic shock) that are required when the patient may not be in a suitable condition to undertake the injection themselves. Glucagon and some of the migraine treatments are normally supplied as a powder that have to be made up with the diluent before the injection which means that they are not suitable for administration by an untrained assistant. In addition, the patient may, or may not be in a fit state to make up the drug let alone administer it. The present device would enable these and similar drugs to be administered in solid dosage form.

Diabetes:—Millions of people worldwide have to inject insulin either daily or several times a day. Most have to use a needle and syringe although new delivery systems such as inhalers and insulin pumps are becoming more popular. The advantage of the new delivery system is that several different types of insulin can be administered in a solid dose form at one tine. This can be done by having two or more short pieces of different insulin formulations in e.g. a drug cassette. This could allow a short as well as a long acting insulin to be injected at the same time and thus reduce the requirement for multiple injections throughout the day.

Although the applications above have been highlighted, the technology is suitable for administering many drugs that are required at the dosage levels capable of being delivered by the system.

SUMMARY OF THE INVENTION

According to a first aspect of the present invention there is provided a drug delivery device (10) comprising:

i) a housing (12);

ii) a means (14) for generating a force capable of pushing a drug (16) from a packaging (18) into a human or animal body;

iii) a means (20) for transmitting said force to push the drug (16) from the packaging (18) into the human or animal body; and iv) a means (38, 42b) for triggering the device.

The numbers are included for illustrative purposes and are not to be construed as limiting.

Such a device can be a reusable device which further comprises a means (22) for receiving a packaged drug (100); and a means (24) for priming the device.

Alternatively the device can be a single use device in which case the packaged drug (100) will be an integral part of the device. Such a device can be provide in a pre primed form which just needs triggering or in a form requiring it to be primed.

A device according to the invention has a number of advantages compared to current needle free devices.

It comprises a small number of components and is therefore cheap to manufacture and assemble. It is also relatively small (currently the same size as a dry marker pen).

In a preferred embodiment of the device, it can only be actuated by inserting a packaged drug and pushing the skin tensioning end of the packaged drug against a solid object. The priming and actuation of the device by pushing the end of the device against the skin ensures that there is a reliable and consistent contact and tensioning of the skin on delivery of the drug. Additionally, by setting the device such that the force required to actuate it is from, for example, 20-30 Newton the force will be too high for a patient to accidentally actuate the device without pushing it firmly against the body's tensioned skin, thereby providing a significant safety feature.

A spring and cap arrangement makes it possible to adjust the actuation force by altering the tension on the spring. By screwing the cap further onto the upper barrel the spring is tensioned and by unscrewing it the force can be reduced. Alternatively, instead of a coil spring as the main power source, the device could incorporate any other type of mechanical spring or a gas spring. In an alternative embodiment the spring could be pre-tensioned during manufacture to avoid having to tension the spring during the drug administration. This would result in a single use device in which case the packaged drug would most likely be an integral part of the device.

The velocity of the impact hammer during administration of the therapeutic agent is less than 20 m/s, more preferably less than 10 m/s, more preferably still less than 5 m/s and most preferably in the order of 0.1-2 m/s. The skilled man will appreciate that the actual speed may vary with the mass of the impact hammer and thus the impact imparted on the delivery dose. As a consequence the therapeutic agent is delivered by a pushing action from the end of the packaged drug rather than by a firing action (as would be the case with a bullet leaving the barrel of a gun).

To ensure that the device actuates automatically when the correct force is applied the hammer has a shaped shoulder region which engages a correspondingly shaped surface in a wall separating the upper and lower barrels. The device will actuate only when the substantially frustoconical sections fully engage. This will be at the same main spring tension every administration and if the administration is aborted before the frustoconical sections engage then the packaged drug can be removed safely without leaving the device primed.

In a preferred embodiment the device can't be primed until the packaged drug is attached thereto since it is the packaged drug that acts against the piston in the device to cause the spring to be tensioned. This makes the device particularly safe. It also means it can't be actuated when not loaded such that an operator can't use the device in a belief they are providing an injection.

In the case of a reusable device a slewing spring returns the impact hammer into it's non axially aligned position at the end of each administration.

Furthermore, because the reusable components of the system (all components except those of the packaged drug) do not come into contact with the target tissue for the drug administration they do need to be sterile.

All components apart from the springs can be moulded making the device cheap to manufacture and the limited number of parts and their ease of assembly keeps assembling costs to a minimum.

A range of custom packaged drugs will fit the delivery device but patients will not be able to easily introduce their own therapeutic compounds into the drug cassettes (as can be done with a needle and syringe).

The device is suitable for both human and veterinary applications.

The device is particularly suitable for self administration of drugs and requires minimal training.

According to a second and related aspect of the invention there is provided a packaged drug (100), for use with a drug delivery device, comprising a packaging (18) containing a drug (16), said packaging (18) comprising a housing (18a, 18b) having a channel (106) running there through and in which is disposed a drive pin or other element (108), a skin piercing means (110; 112), and the drug (16), said housing (18a, 18b) comprising i) a region (102) allowing the packaged drug (100) to be slidably mounted to the drug delivery device (10); and ii) an end (104) adapted to engage and tension the skin.

In the case of a drug splinter the skin piercing means and the drug may be one of the same.

Preferably the drug is disposed between the drive pin and the skin piercing means.

Preferably the packaged drug takes the form of a disposable end cap, cartridge, cassette or carousel, containing a single or multiple doses of the drug.

Preferably the region for engaging the packaged drug to the drug delivery device in a slidable manner additionally comprises a means for positively locking it to the device such that it can still slide within the device but will not fall out under gravity. Such a means might be a sprung pin or spigot which exerts a frictional force against the device or a mechanism whereby the packaged drug is inserted in a particular orientation and turned so that it is precluded from being removed unless it is turned back into the position in which it was allowed to enter.

In a first embodiment the packaged drug houses either a pioneer projectile in combination with a drug in a contained state, more preferably a solid, or a drug splinter (a single solid entity).

In a second embodiment the piercing means comprises a needle with two sharp ends, one for puncturing the skin and the other for puncturing a membrane of a receptacle containing the drug, the drug being released into the needle from where it drains out into the body through the needle. The drug is preferably a liquid and is contained in the receptacle which is disposed in the channel. Advantageous features of the device include a spacer between the membrane piercing end of the needle and the membrane of the drug containing receptacle to prevent the needle coming into contact with the membrane prior to actuation. The spacer is either resilient or compressible and may be supported by a plate attached to the needle. The receptacle is preferably sealed by the drive pin or other like element.

In a third embodiment the packaged drug may contain a drug in any state (e.g. solid, semi solid or liquid), the actuation of the device causing, in a two step operation, first the entry of a pioneer projectile and only then the release of the drug from a thin walled tube. Release of the drug may optionally require the breaking of a membrane supporting the drug in the tube.

In a variation of this embodiment the pioneer projectile, which is located immediately in front of the thin tube, could be replaced by a retractable needle tip which is, or is integral with, the thin walled tube. As per embodiment 1 and 2 described above, the thin walled tube could have a compression spring or other resilient member associated therewith to withdraw the thin walled tube following the injection.

A particularly clever feature of this embodiment is the form of the drive pin or element which has a plurality of flexible or frangible arms, in the embodiment illustrated two, extending from its main body. These arms extend outwards (splay) when they ride over a ramped surface provided on the housing, are forced away from the body, and ride over a lip on the tube as a consequence of the flex or frangibility. In consequence the body of the drive pin or element can move down the tube. This arrangement facilitates a two step operation whereby in a first step the drive pin or element acts on the tube causing it to move and push the pioneer projectile into the skin, and then, and only when the first step is complete, the arms are caused to splay and/or snap thereby allowing the drive pin body to push the drug contents from the tube. In the case where the arms are frangible the arms will snap off as a result of an area of weakness formed about the shoulder region and fall into a cavity about the ramped region. A frangible system has two advantages: firstly it should ensure full injection occurs, and secondly it will mean the packaged drug can't be re-used. The ramp is preferably "circular" in design, taking the form of a frustoconical surface. This has the advantage that it can be easily moulded and does not require the arms to be orientated for contact.

Depending on the diameter of the thin walled tube and the viscosity of the therapeutic compound, the thin walled tube may need to be sealed, or partially sealed to avoid premature loss of the drug. However the action of the drive pin body will be sufficient to break any seal allowing the drug to be released and pushed into the patient.

An advantage of the packaged drugs exemplified is their small cheap sub-assembly. They are also easy to handle and place into the device prior to administration. Their size also facilitates easy storage in for example refrigerators.

The packaged drug may be sealed in a foil pouch or the like to prevent ingress of, for example, moisture, oxygen, light, bacteria or other drug degrading or contaminating agents.

In those embodiments having a pioneer projectile the tip will, in most instances, be positioned a few millimeters from the end of the drug cassette so that it is moving when it strikes the target tissue.

Preferably the end adapted to engage and tension the skin comprises one or more projections about the channel exit, most preferably in the form of an annular ring, as such an arrangement most effectively tensions the skin.

A retention system may advantageously be employed to hold the drug and pioneer projectile in place in the channel. This might be achieved by, for example, extruding or moulding the drug and/or pioneer projectile with a number of small splines or other features along their outer surface. These splines or other features would provide a frictional fit but would not prohibit the drug from being administered. Alternatively, the channel of the packaging might have a small feature, such as, for example, a retaining bump or other projection over which the pioneer projectile and drug have to be pushed.

A tamper or use evident seal or other indicator means may additionally be placed over the top end of the packaged drug so that when e.g. the seal is broken it is obvious that the packaged drug has not been interfered with and/or is spent.

Additionally or alternatively a seal may be place over the exit of the channel of the packaged drug. It would be preferable to remove this seal prior to administration of the drug but it would best be designed such that the administration could be carried out through the seal just in case it wasn't removed by the user.

According to yet a further aspect of the invention there is provided a method of delivering a drug to a human or animal using a device and/or packaged drug according to the invention.

The various aspects of the invention will now be described by way of example only with reference to the following Figures and Examples.

BRIEF DESCRIPTION OF THE DRAWINGS

FIG. 1 is one embodiment of a reusable device according to one aspect of the invention with one embodiment of a packaged drug according to another aspect attached thereto, the device being shown pre-use;

FIGS. 2a, b, and c illustrate a device substantially similar to the device illustrated in FIG. 1 in:

Figure 3:
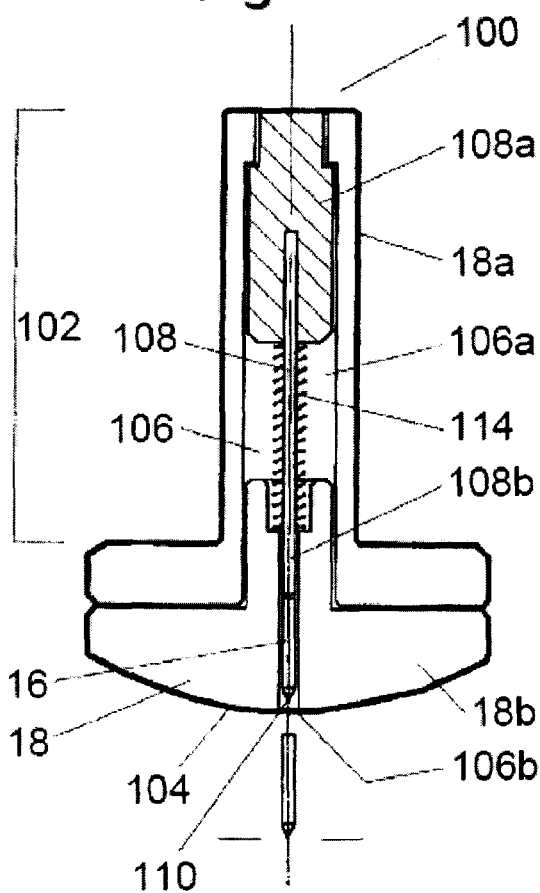
Figure 4:
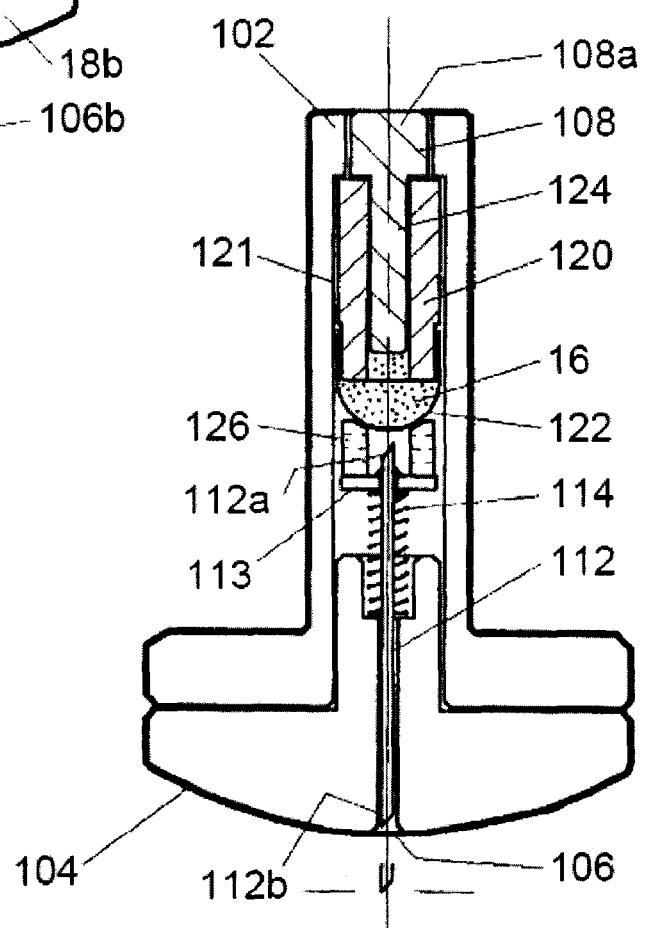
Figure 5:
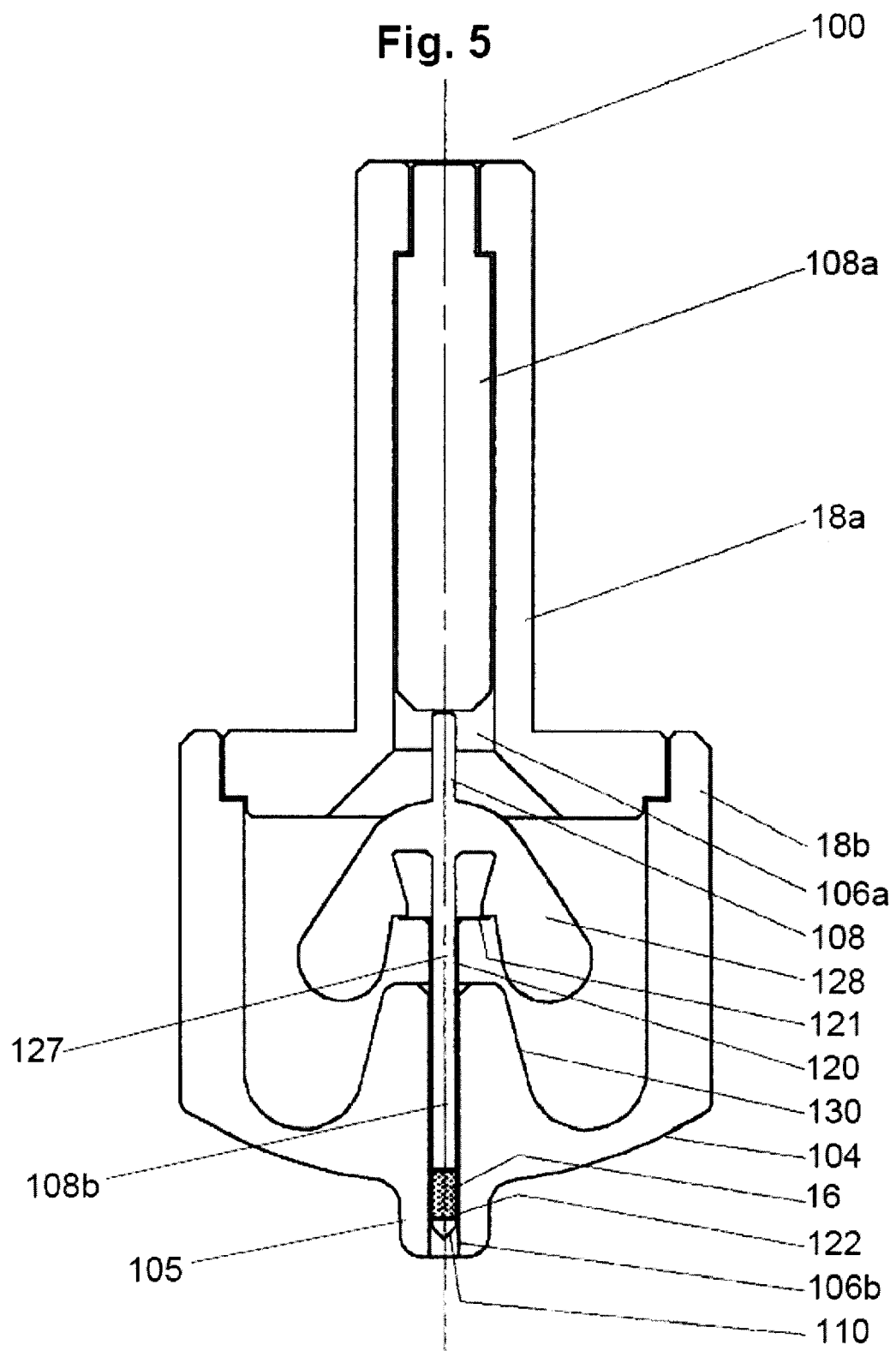

a) its assembled form b) at the point where it is fully primed and about to self actuate; and c) in its post actuation position;

FIG. 3 is a packaged drug according to one aspect of the invention in which the drug is in a solid or otherwise contained form and follows a pioneer projectile;

FIG. 4 is a packaged drug according to another aspect of the invention in which the drug is in a liquid form and is released and injected via a retractable needle; and FIG. 5 is a packaged drug according to yet a further aspect of the invention in which the packaging is adapted to hold a drug in a solid or liquid form and in which the end of the packaging is modified to be particularly well adapted to skin tensioning.

DETAILED DESCRIPTION

FIG. 1 illustrates a (reusable) drug delivery device (10), with a packaged drug (100) fitted thereto. It comprises very few components. They include i) a housing (12);

ii) a means (14) for generating a force capable of pushing a drug (16) from a packaging (18) into a human or animal body;

iii) a means (20) for transmitting said force to push the drug (16) from the packaging (18) into the human or animal body;

iv) a means (22) for receiving a packaged drug (100);

v) a means (24) for priming the device; and vi) a means (38,42b) for triggering the device.

In the embodiment shown the device is primed and triggered in a single action.

The delivery device (10) which may be absent of the packaged drug (100) is spring powered. It can deliver the drug or a formulation containing a therapeutic compound (hereafter drug) in a solid, semi-solid or liquid form. By altering the form of the packaged drug (100) the device can be used to either deliver drugs through a retractable needle (FIG. 4), or behind a "pioneer projectile" (FIGS. 3 and 5). It can also be used to deliver a solid drug splinter.

Looking at the device in more detail it comprises a number of components which are readily assembled and easily sterilised making manufacture cheap.

The body of the device comprises a three part housing (12) comprising a first housing component (12a) defining an upper barrel (28) which houses the force generating means (14), a second housing component (12b) defining a lower barrel (30) which houses the packaged drug (100) and the means (20) for transmitting the force to push the drug (16) from its packaging (18). The first and second housing components (12a; 12b) connect to one another, and a third housing component (12c), which preferably takes the form of a screw cap (32), fits over the end of the first housing component to close off the upper barrel (28).

Within the upper barrel (28) is fitted the means (14) for generating the force capable of pushing the drug (16) from its packaging. In the embodiment shown this takes the form of a mechanical coil spring which can generate a force of from about 10-40 N, more preferably 15-35 N and most preferably 18-31 N. The spring is connected at its lower end to a spring follower (36) which is slidably mounted in the upper barrel (28). Above the spring is a compression bar (34) which provides a contact surface against which the spring can act. By screwing or unscrewing the cap (32) from the housing component (12a) the spring can be caused to compress or relax thereby providing a means for adjusting the force that can be generated by it. In FIG. 1 the spring is shown at minimum pre-load.

The upper barrel (28) and lower barrel (30) are separated from one another by a wall (42) with a communicating aperture (43) therein and it is on the upper surface (42a) of this wall that the spring follower (36) sits. The means (20) for transmitting the force generated by the spring takes the form of an impact hammer one end (20a) of which passes through the communicating aperture (43) where it contacts spring follower (36). In use the uppermost end (20a) of the impact hammer slides through the communicating aperture (43) pushing the spring follower (36) up the upper barrel (28) causing the spring to be compressed thus priming the device.

Within the lower barrel is housed not only the majority of the impact hammer (20), but a slewing spring (44) and a sliding piston (48) having an aperture (46) therein, such that the lower barrel can operatively communicate with the packaged drug (100) which is secured to the device via the receiving means (22) provided at the devices lowermost end (49).

The slewing spring functions to draw the longitudinal axis of the impact hammer off centre (FIG. 2a) in the devices rest position. However, the hammer is adapted by way of a shaped shoulder region (38), (which in a preferred embodiment is substantially frustoconical, as illustrated) to be drawn into axial alignment with the aperture (46) in the sliding piston, against the action of the slewing spring (44), such that when it is fully primed the device automatically actuates. Accordingly the lowermost surface (42b) of the wall (42) is shaped to receive the shaped shoulder region (38) of the impact hammer and cause the impact hammer to be axially aligned with the aperture (46) in the sliding piston (48) such that it is driven by the spring (14) through the aperture (46) in the sliding piston (48) where it contacts a drive pin (108) or other element causing the drug (16) to be pushed out of its packaging (18) into the human or animal. In contrast with the FIG. 1 embodiment it should also be noted that the end (20a) of the impact hammer graduates to a point (being substantially conical) and is seated in a similarly shaped recess (36a) in the spring follower (36). The shaping of the hammer end (20a) and the provision of the similarly shaped recess (36a) in the spring follower (36) further improves reliability of actuation.

Figure 2A:
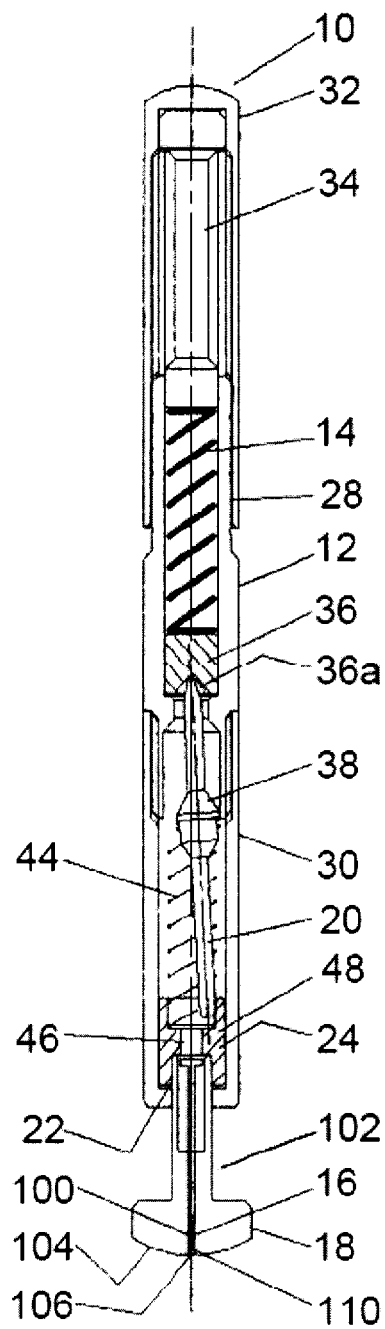
Figure 2B:
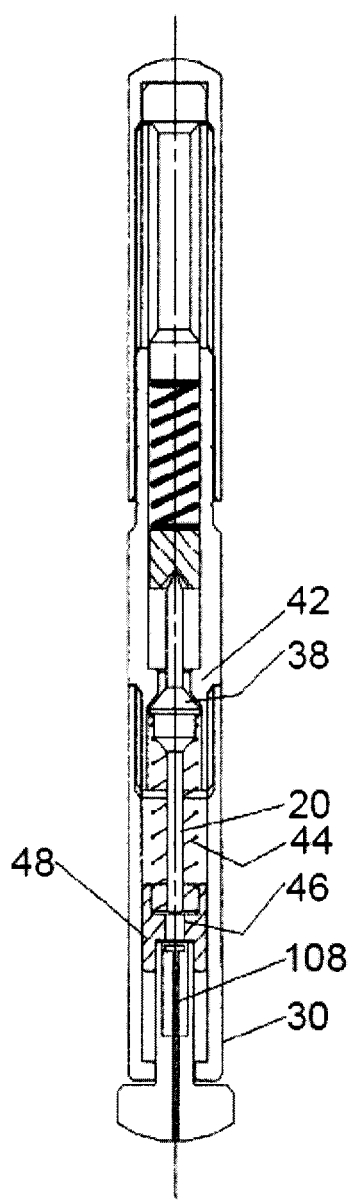
Figure 2C:
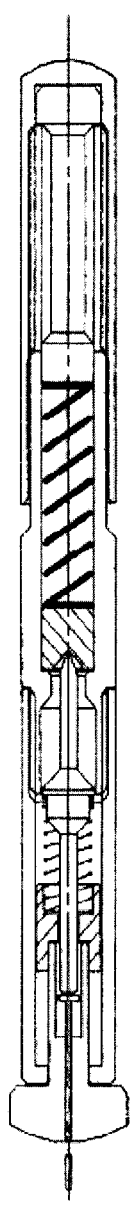

By comparison of FIG. 2a with FIGS. 2 b and c it will be apparent that once a packaged drug (100) has been attached to the lower most end (49) of the device (10) it can be actuated by a user holding the device about it's housing (12) and pressing the device (10) firmly against the patients skin. This causes first the skin to be tensioned and then the packaged drug (100) slides up the lower chamber (30) pushing the piston (48) which in turn pushes the impact hammer (20). As it does so the upper end (20a) of the impact hammer pushes against the spring follower (36) causing the spring (14) to be compressed until the necessary drive force is reached. This is at the point illustrated in FIG. 2b. At this point the shaped shoulder region (38) is drawn into the shaped lowermost surface (42b) of wall (42), the action of the slewing spring (44) is countered, the spring (14) is fully charged and the impact hammer (20) axially aligned with the aperture (46) in the sliding piston (48) such that it will automatically actuate, the spring (14) forcing the impact hammer (20) through the aperture (46) in the piston (48) causing it to push the drive pin (108) which in turn, depending on the mechanism employed in the packaged drug (100) (see FIGS. 3 to 5) causes the drug to be dispensed into the human or animal. Significantly the longitudinal axis of the impact hammer can't be aligned with the aperture (46) in the sliding piston (48) until it reaches the set actuating force which is set to coincide with the point at which the shaped shoulder region (38) contacts the shaped lowermost surface (42b) of wall (42) thus providing a safety mechanism against accidental actuation. When it reaches this point triggering is automatic and the device is actuated (FIG. 2c).

It should be noted that on actuation the hammer moves only a short distance, less than 10 mm, more preferably less than 5 mm and typically about 3 mm before impacting the drive pin and therefore moves (say) approx 5 mm before the pioneer projectile strikes the skin. This means that the maximum force and impact are all in the first few millimetres of travel, when the maximum force is required to pierce the skin. Through the rest of the delivery, the force is reducing as the main spring power is diminishing and also the slewing spring is being compressed (FIG. 2c). This means that the force tapers off during the second half of the delivery when less force is required.

Therefore the force profile through the whole delivery matches the requirements i.e. a high force and impact to pierce the skin and then a reduced force to push the injectate into the skin In the case of a reusable device the packaged drug is removed from the device and discarded. The slewing spring will assist in this action. As the packaged drug (100) is removed from the device the slewing spring (44) acts to draw the impact hammer (20) so that it is not axially aligned with the aperture (46) in the piston (48) and the device (10) is ready to receive a new packaged drug.

Such a device can be used to dispense a drug in a variety of different forms depending on how it is packaged.

To demonstrate the versatility of the device three different designs (FIGS. 3, 4 and 5) of packaged drug (100) are illustrated as suitable for use with the device. All three embodiments illustrate the dispensing of a single dose but the skilled man will appreciate that multi-doses could also be dispensed simultaneously or sequentially with the device of the invention. Similarly, the device could be produced in a pre-primed form with the packaged drug forming an integral part of the device.

Referring to FIG. 3, in one embodiment the packaged drug (100) takes the form of an end piece which is adapted to be slidably mountable in the device (10). The packaging (18) takes the form of a two-piece housing (18a, 18b), thereby simplifying construction and assembly. A first housing element (18a) is the shape of a hollow inverted "T" and comprises a region (102) (the stem of the "T") which serves in use to slidably engage the device (10) allowing the packaged drug to slide up the lower chamber (30) of the device (10), and a "cross piece" against which the second element (18b) abuts. A central channel (106a) runs through the middle of the stem exiting at the crosspiece. The second element (18b) comprises an end (104) which is shaped to tension the skin. The second element (18b) is also substantially the shape of an inverted T and has a channel (106b) running down the centre axis of the inverted T. The respective channels (106a, 106b) communicate with one another to form a single channel (106) which runs right through the packaging (18). The channel (106b) houses a pioneer projectile (110) and the drug (16) or a drug splinter (effectively 110,16), the skin contacting end of which is set a few millimetres in from the skin tensioning surface of the device to ensure it is moving at the requisite speed when it contacts the skin. It also houses the lower end (108b) of the drive pin (108). At the end remote from the skin tensioning surface the channel (106b) opens out to house a resilient member e.g. a spring (114). The placing of a resilient member under the head (108a) of the drive pin allows the drive pin to be withdrawn back into the housing immediately after actuation. The drive pin (108) is slidably mounted in the channel (106) so that when the head is depressed by the hammer of the device the drive pin moves down the channel pushing the pioneer projectile and drug (110, 16) from the channel (106b) into the human or animal body. The pioneer projectile (110) and drug (16) are held in place in the channel (106b) by, for example, a breakable membrane (not shown) or appropriate frictional means e.g. one or more markings or splines on either the pioneer projectile, drug and or channel (106b) surface.

The packaged drug illustrated in FIG. 3 is suitable for the injection of a "contained" drug behind a pioneer projectile which can penetrate the skin and create a channel into which the drug is pushed as described in UK application no 0121914.6. This type of packaged drug is also suitable for the administration of drug splinters or rods of a solid therapeutic compound which have a sharp tip as per WO 94/22423. The therapeutic compound or therapeutic compound and tip are initially located in the channel (106) of the packaging (18). The distal end (108b) of the drive pin may or may not be in contact with the uppermost end of the therapeutic compound prior to actuation. When the drive pin head (108a) is struck by the impact hammer the drive pin (108) pushes the therapeutic compound (and pioneer projectile, if included) into the target tissue.

The end of the drive pin may just penetrate the outer layers of the skin to ensure that the therapeutic compound is completely delivered into the skin. Alternatively, the packaged drug may include a short rod (or rods) of a placebo or pharmaceutical compound between the end of the drive pin and the therapeutic compound, which can be used to push the therapeutic compound fully into the skin. In this case it would not matter if the placebo rods entered the skin but it would ensure that the drive pin did not have to penetrate the skin. The benefits of this are that the drive pin would not be left protruding from the packaged drug following the administration and would not be contaminated with bodily fluids and it would therefore not pose a health risk in terms of disposal. An alternative is to include a piece of rubber or foam, or as illustrated a light spring (114), under the head (108a) of the drive pin to ensure that the tip of the drive pin is withdrawn into the spent packaging after administration.

FIG. 4 illustrates an alternative design of a packaged drug for use with a device according to the invention. The packaged drug comprises a two piece housing (18a, 18b) which is identical to that of the FIG. 3 embodiment. This simplifies manufacture as the housing components can be used for a packaged drug which is solid (as per the FIG. 3 embodiment) or one which is liquid. In order to be adapted to dispense a liquid a needle (112) sits in the channel (106), it's lower end (112b) being in the channel (106b) of housing component (18b) and its upper end (112a) extending into the channel (106a) of housing component (18b). The needle (112) is obliquely cut at both ends to provide sharp points. Attached to the upper end (112a) of the needle is a support plate (113) on which is seated a resilient or compressible spacer (126) which extends above the tip of the upper end (112a) of the needle. Seated on the spacer (126) immediately above the tip of the needle (112) is a liquid drug containing receptacle (120). The receptacle comprises one or more side walls (121) and a puncturable base (122) which together define a receptacle cavity which is filled with the drug (16) through an opening (124). The receptacle is sealed by a drive pin or element (108) which sits in the receptacle opening (124).

In use the hammer of the drug delivery device contacts the drive element head (108a) causing the receptacle to be pushed down the channel (106a) of the housing element (18a). The spacer (126) is compressed causing the needle to puncture the base (122). Consequently the needle (112) is filled by some of the drug contents (16) of the receptacle thereby expelling air from the needle prior to piercing of the skin and delivery of the drug. The force exerted on the support plate (113) forces the needle into the skin where the liquid drug contents (16) drain into the human or animal through the tract formed by the needle (112). As the user of the device removes the device from the skin, the drug package is pushed substantially out of the end of the device by the action of the slewing spring, and the needle is withdrawn into the drug package by the action of the spring (114).

In yet a further embodiment, and as illustrated in FIG. 5 there is a packaged drug (100) which is adapted to hold a drug (16) in any state, liquid, semi solid or solid. As in the previous embodiments the housing (18) preferably takes the form of a two piece housing (18a, 18b) although in this case the housing elements are shaped differently. In channel (106b) of the second housing element (18b) is housed a pioneer projectile (110) and the lowermost part of a drug containing receptacle (120) in the form of a thin walled metal tube which is sealed with a breakable membrane (122). The tube terminates at it's uppermost end in a lip (121) on which rest a pair of flexible arms (128) of a drive element (108). The receptacle is sealed by the drive element (108). At the end remote from the skin tensioning surface of the second housing element (18b) is a ramped surface (130). The uppermost part of the drug containing receptacle (120) and the drive element (108) sit in a cavity between the housing elements (18a, 18b) and which can be considered an extension of channel (106a) formed in the first housing element (18a). The end (104) in this embodiment is particularly well suited to skin tensioning and includes an annular ring (105) located immediately about the channel (106) exit. The annular ring in this embodiment is about 3 mm in diameter (including the channel which is about 1 mm in diameter) and depth. By way of comparison the end (104) has a diameter of about 16 mm. The depth and width need not be 3 mm by 3 mm but should generally be in the range 1.5 mm to 6 mm. Any more than this and it may cause pain and bruising and any less than this and it may not adequately tension the skin. This annular ring which may be a whole ring or a broken ring comprising a number of projecting elements disposed in a substantially annular fashion about the channel exit could be a feature of any embodiment. To simplify construction in this embodiment the drive pin head (108a) is produced as separate component to the lower and elongate end (108b) of the drive pin.

In use the hammer of the drug delivery device contacts the drive element head (108a) causing the receptacle to be pushed down the channel (106b) as a consequence of the force exerted by the flexible arms (128) of the drive element (108) against the lip (121) of the receptacle (120). This causes the pioneer projectile (110) to be pushed into the patient. Once the pioneer projectile has entered the patient the flexible arms (128) of the drive element (108) contact the ramp surface (130) of the second housing element (18b) and are caused to flex apart and ride over the lip (121) and/or snap. As a consequence the lower part (108b) of the drive element is able to move down the receptacle (120) pushing the drug (16) contents out into a tract formed by the pioneer projectile (110). Preferably the end of the receptacle which takes the form of a thin walled tube just enters the skin before the drug is delivered. This ensures that if a liquid drug is used the drug follows the pioneer projectile into the skin rather than escaping along the skin surface.

The main advantage of the FIG. 5 embodiment is for the injection of liquids as it ensures that the liquid is contained during the administration and is guided by the thin walled metal tube into the target tissue. However, the drug contents need not be restricted to liquids.

A feature of the device illustrated which further distinguishes it from other hand powered systems is that the force generated by the spring is the delivery force and there is substantially no additional force generated by the operator due to the gradual priming and instantaneous actuation when the device reaches the delivery force set.

In contrast devices which include a break tab or other snap means to actuate the device can't have the force carefully controlled and as a consequence the greater the force exerted by the user the greater the velocity of impact by the drug with the skin.

With the system detailed in this application the hand force compresses the main spring to a preset point at which the drug package is inserted to virtually its maximum point within the device. At this point the actuation takes place and the predetermined spring strength delivers the drug. Any extra force by the hand is dissipated over the whole of the area of the end of the device.

An alternative way of viewing this is to consider the skin as a sponge. In devices utilising snap tabs, when the snap tabs are broken all the force by the hand is pushing the drug and the resilience of the skin will start to push the bottom half of the device (part not held in hand) back towards the hand. This may result in a less good seal with the skin and, in theory, if the hand force stops immediately the snap tabs are broken then the drug would never be pushed from the device—they rely on the inertia in the hand to make the injection. In practice this means that the user pushes and pushes and then suddenly the tabs break and the device is pushed into the target possibly causing pain and bruising with the device. In the present injection the skin is compressed by a steady hand force. At the point of actuation the main spring controls the delivery of the drug and the hand maintains (but does not suddenly increase) the force on the skin to ensure a good contact with the skin. If at any point before actuation the sensation on the skin is painful then the injection site can be altered or the injection aborted rather than causing further pain and/or bruising.

Devices of the type described have been demonstrated by the applicant to be capable of delivering a drug as demonstrated by the following examples:

EXAMPLES

Initial experiments were carried out with non pharmaceutical materials to demonstrate the delivery concept. These experiments comprised the following:

Example 1

Drug Splinters

A rod of 0.9 mm diameter pencil lead was broken to lengths of approximately 6 mm and a point was sanded on one end of each length and a flat on the other to create solid splinters. The splinters were placed in the drug package shown in FIG. 3 and successfully administered to pig skin using a prototype delivery system.

Example 2

Pioneer Projectile Followed by a Solid Rod

The same pencil lead detailed in example 1 above was cut into short lengths of approximately 3 mm in length. These had a point sanded on one end and a flat on the other end to create pioneer projectiles. Further rods of the same pencil lead were cut at approximately 4 mm in length and had both ends sanded flat. When a pioneer projectile and a solid rod were placed in a drug package as shown in FIG. 3 they were successfully administered to pig skin using a prototype delivery system.

Example 3

Pioneer Projectile Followed by a Soft Rod

A soft rod of wax was extruded through a die and rods of approximately 4 mm in length were cut with a flat at each end. Further sections were cut with a point at one end and a flat at the other end. When a pointed section (identical in shape and size to the splinter used in example 1) was administered to pig skin using a drug package as shown in FIG. 3 the wax did not pierce the skin but was flattened on the skin surface. When a rod of the same waxy material was placed behind a pioneer projectile used in example 2 and administered to pig skin using a drug package as shown in FIG. 3 then both the pioneer projectile and the waxy material were successfully delivered into the tissue. The wax material used for this experiment could easily be squashed between a finger and a thumb.

Example 4

Pioneer Projectile Followed by Solid Beads

Beads of diameters 0.5-0.75 mm were placed in a drug package, as shown in FIG. 3, behind a pioneer projectile as detailed in example 2. The pioneer projectile and all the beads were successfully administered to pig skin using a prototype delivery system.

The experiments outlined above demonstrated that a range of different materials could be delivered behind a solid pioneer projectile. Ideally it is preferred that the pioneer projectile is manufactured from pharmaceutical grade compounds that will dissolve in the target tissue. Two processes have been used to produce such pioneer projectiles as outlined below:

Example 5

A hot melt of sugars is produced which can then be moulded into the correct form for a pioneer projectile or extruded to produce long rod. If an extrusion process is used then the pioneer projectiles can be cut to shape from the soft extrudate or the sharp ends of the pioneer projectile can be formed when the extrudate has solidified. This process produces a material similar to a boiled sweet which can be very hard and incorporate a sharp point on one end.

Example 6

A mix of powders is produced using pharmaceutical grade sugars together with a hardening agent such as polyvinylpyrolidone (PVP). The powder blend is extruded through a die to produce a long rod of the compound. Some blends require a lubricant to facilitate the extrusion and binding process such as water or ethanol. The pioneer projectiles are formed by cutting the long rod into short sections. This process can be facilitated by using a hot knife. If necessary, the point or flat end of the pioneer projectile can be created by sanding or filing a short rod of the extrudate.

The invention claimed is:

1. A drug delivery device comprising:
 (i) a housing including an upper barrel and a lower barrel;
 (ii) a means for generating a force capable of pushing a drug from a packaging into a human or animal body;
 (iii) said upper barrel being at one end of the device;
 (iv) said upper barrel housing the force generating means;
 (v) said lower barrel (30) being at a second end of the device remote from said upper barrel which includes a means (20) for transmitting said force to push the drug (16) from the packaging (18) into the human or animal body, a sliding piston (48) and a means (22) for slidably receiving a packaged drug (100) configured such that a packaged drug attached thereto can slide within the device and act against said piston in the device to prime it;
 (vi) a means for triggering the device wherein said force generating means and said force transmitting means are configured to push the drug from the packaging into the human or animal body at a velocity of less than 20 m/s;
 (vii) said lower barrel being in operative communication with said upper barrel and said packaged drug; and
 (viii) wherein the packaged drug is slidably disposed in said lower barrel and comprises a packaging containing a drug, said packaging comprising a two-piece housing having a channel running therethrough in which is disposed a drive pin or other element, a skin piercing means and the drug; said two-piece housing further comprising i) a region allowing the packaged drug to be slidably mounted to the drug delivery device at a receiving means; and ii) an end adapted to engage and tension the skin; and
 (ix) a resilient means below or otherwise in association with the drive pin or other elements to ensure the drive pin is withdrawn after use.

2. A drug delivery device comprising:
 (i) a housing including an upper barrel and a lower barrel;
 (ii) a means for generating a force capable of pushing a drug from a packaging into a human or animal body;
 (iii) said lower barrel (30) being at an end remote from said upper barrel which includes a means (20) for transmitting said force to push the drug (16) from the packaging (18) into the human or animal body, a sliding piston (48) and a means (22) for slidably receiving a packaged drug (100) configured such that a packaged drug attached thereto can slide within the device and act against said piston in the device to prime it; and (iv) a means for triggering the device wherein said force generating means and said force transmitting means are configured to push the drug from the packaging into the human or animal body at a velocity of less than 20 m/s;

(v) the means for generating the force capable of pushing the drug is a spring; and (vi) a spring follower.

3. A drug delivery device as claimed in claim 2 wherein the means for transmitting the force comprises a substantially conical end and the spring follower has a correspondingly shaped recess in the underside thereof.

4. A drug delivery device comprising:
(i) a housing including an upper barrel and a lower barrel;
(ii) a means for generating a force capable of pushing a drug from a packaging into a human or animal body;
(iii) said upper barrel being at one end of the device;
(iv) said upper barrel housing the force generating means;
(v) said lower barrel (30) being at a second end of the device remote from said upper barrel which includes a means (20) for transmitting said force to push the drug (16) from the packaging (18) into the human or animal body, a sliding piston (48) and a means (22) for slidably receiving a packaged drug (100) configured such that a packaged drug attached thereto can slide within the device and act against said piston in the device to prime it;
(vi) a means for triggering the device wherein said force generating means and said force transmitting means are configured to push the drug from the packaging into the human or animal body at a velocity of less than 20 m/s;
(vii) said lower barrel being in operative communication with said upper barrel and said packaged drug;
(viii) wherein the packaged drug is slidably disposed in said lower barrel and comprises a packaging containing a drug, said packaging comprising a two-piece housing having a channel running there through in which is disposed a drive pin or other element, a skin piercing means and the drug; said two-piece housing further comprising i) a region allowing the packaged drug to be slidably mounted to the drug delivery device at receiving means; and ii) an end adapted to engage and tension the skin; and
(ix) wherein the packaged drug and striker are slidably mounted in the device such that the device can be primed by pushing the device against the skin.

5. A drug delivery device comprising:
(i) a housing including an upper barrel and a lower barrel;
(ii) a means for generating a force capable of pushing a drug from a packaging into a human or animal body;
(iii) said upper barrel being at one end of the device;
(iv) said upper barrel housing the force generating means;
(v) said lower barrel (30) being at a second end remote from said upper barrel which includes a means (20) for transmitting said force to push the drug (16) from the packaging (18) into the human or animal body, a sliding piston (48) and a means (22) for slidably receiving a packaged drug (100) configured such that a packaged drug attached thereto can slide within the device and act against said piston in the device to prime it;
(vi) a means for triggering the device wherein said force generating means and said force transmitting means are configured to push the drug from the packaging into the human or animal body at a velocity of less than 20 m/s;
(vii) said lower barrel being in operative communication with said upper barrel and said packaged drug; and
(viii) wherein the packaged drug is slidably disposed in said lower barrel and comprises a packaging containing a drug, said packaging comprising a two-piece housing having a channel running there through in which is disposed a drive pin or other element, a skin piercing means and the drug; said two-piece housing further comprising i) a region allowing the packaged drug to be slidably mounted to the drug delivery device at receiving means; and ii) an end adapted to engage and tension the skin; and
(ix) wherein the means for transmitting the force is a striker;
(x) wherein a region of the striker is shaped to fit a correspondingly shaped surface in a wall separating said upper and lower barrels defined by the housing such that the striker is aligned to strike the drive pin or other element in the packaged drug on actuation
(xi) wherein the striker comprises a substantially frustoconical shoulder region which engages a substantially frustoconical surface in the wall separating said upper and lower barrels defined by said housing; and
(xii) wherein the sliding piston has an aperture therein and the device comprises a slewing spring and the striker, all housed in said lower barrel, the device being triggered by the sliding of the piston up said lower barrel until the shoulder region of the striker engages the shaped surface and aligns the striker with the aperture in the sliding piston such that the striker moves down the aperture under the action of the force generating means.

6. A drug delivery device as claimed in claim 5 wherein the device is primed and actuated by a single action.

7. A device as claimed in claim 6 wherein pushing the packaged drug up the lower barrel with sufficient force causes the device to be primed and actuated.

8. A device as claimed in claim 6 wherein the action of pushing the packaged drug up the lower barrel with sufficient force causes the sliding piston to move up the lower barrel thereby causing the striker to be pushed up the lower barrel out of a first position in which it is not axially aligned with the aperture in the sliding piston which operatively communicates with the packaged drug and at the same time acts on a spring follower in the upper barrel causing the spring to be compressed and the device primed such that when the required delivery force is generated the striker is axially aligned with the aperture of the sliding piston and is thus actuated such that the spring acts through the spring follower and striker upon the drive pin or a like element in the packaged drug to deliver the drug into the human or animal body.

9. A packaged drug, for use with a drug delivery device, comprising a packaging containing a drug, said packaging comprising a housing having a channel running there through an in which is disposed a drive pin or other element, a skin piercing means, and the drug, said housing further comprising i) a region allowing the packaged drug to be slidably mounted to the drug delivery device; and ii) an end adapted to engage and tension the skin; and
further comprising a resilient means below the drive pin head to ensure the drive pin is withdrawn after use.

10. A packaged drug, for use with a drug delivery device, comprising a packaging containing a drug, said packaging comprising a housing having a channel running there through an in which is disposed a drive pin or other element, a skin piercing means, and the drug, said housing further comprising i) a region allowing the packaged drug to be slidably mounted to the drug delivery device; and ii) an end adapted to engage and tension the skin; and further comprising a receptacle having a breakable base and being sealed by the drive pin or other element which drive pin or other element comprises an elongate body and a plurality of flexible arms.

11. A packaged drug as claimed in claim 10 in which the arms of said element, in use, ride over one or more ramped surfaces provided on the housing such that they are displaced and/or break away from the elongate body so the elongate body of the drive pin can travel down the receptacle, causing the drug to be expelled from the base of the receptacle which breaks under the pressure exerted thereon.

12. A packaged drug as claimed in claim 10 further comprising a pioneer projectile below the base of the receptacle.

13. A packaged drug, for use with a drug delivery device, comprising a packaging containing a drug, said packaging comprising a housing having a channel running there through an in which is disposed a drive pin or other element, a skin piercing means, and the drug, said housing further comprising i) a region allowing the packaged drug to be slidably mounted to the drug delivery device; and ii) an end adapted to engage and tension the skin; and wherein a placebo is disposed behind the drug.

* * * * *